United States Patent
Maitland et al.

(10) Patent No.: US 7,611,524 B1
(45) Date of Patent: Nov. 3, 2009

(54) GUIDE WIRE EXTENSION FOR SHAPE MEMORY POLYMER OCCLUSION REMOVAL DEVICES

(75) Inventors: Duncan J. Maitland, Pleasant Hill, CA (US); Ward Small, IV, Livermore, CA (US); Jonathan Hartman, Sacramento, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 251 days.

(21) Appl. No.: 11/238,018

(22) Filed: Sep. 27, 2005

(51) Int. Cl.
*A61B 17/08* (2006.01)
(52) U.S. Cl. .................... 606/157; 606/113
(58) Field of Classification Search .............. 606/200, 606/108, 151, 153, 157, 159, 113, 114, 127
See application file for complete search history.

(56) References Cited

U.S. PATENT DOCUMENTS

| | | | |
|---|---|---|---|
| 6,425,909 B1 * | 7/2002 | Dieck et al. ................. 606/200 |
| 6,692,509 B2 | 2/2004 | Wensel et al. |
| 6,740,094 B2 * | 5/2004 | Maitland et al. ............ 606/108 |
| 6,773,448 B2 * | 8/2004 | Kusleika et al. ............ 606/200 |
| 6,818,006 B2 * | 11/2004 | Douk et al. ................. 606/200 |
| 6,932,830 B2 * | 8/2005 | Ungs ........................... 606/200 |
| 2002/0095169 A1 * | 7/2002 | Maitland et al. ............ 606/194 |
| 2003/0171741 A1 | 9/2003 | Ziebol et al. |
| 2003/0195554 A1 * | 10/2003 | Shen et al. .................. 606/200 |
| 2003/0236533 A1 * | 12/2003 | Wilson et al. ............... 606/127 |
| 2004/0133231 A1 | 7/2004 | Maitland et al. |
| 2005/0085846 A1 * | 4/2005 | Carrison et al. ............ 606/200 |

\* cited by examiner

*Primary Examiner*—Kevin T Troung
(74) *Attorney, Agent, or Firm*—Eddie E. Scott; John H. Lee

(57) ABSTRACT

A flexible extension for a shape memory polymer occlusion removal device. A shape memory polymer instrument is transported through a vessel via a catheter. A flexible elongated unit is operatively connected to the distal end of the shape memory polymer instrument to enhance maneuverability through tortuous paths en route to the occlusion.

20 Claims, 1 Drawing Sheet

GUIDE WIRE EXTENSION FOR SHAPE MEMORY POLYMER OCCLUSION REMOVAL DEVICES

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to medical devices and more particularly to a shape memory polymer medical device.

2. State of Technology

United States Patent Application No. 2002/0095169 by Duncan Maitland et al published Jul. 18, 2002 for a shape memory polymer actuator and catheter provides the following state of technology information, "A catheter with a shape memory material is transported to the site of the matter to be removed. The shape memory material is passed through or around the matter. Heat is utilized to activate the shape memory material and expand the shape memory material. By withdrawing the catheter and the shape memory material through said vessel the matter is carried from the vessel."

United States Patent Application No. 2004/0133231 by Duncan Maitland et al published Jul. 8, 2004 for a shape memory polymer actuator and catheter provides the following state of technology information, "The system uses heat to activate a shape memory material. The shape memory material will change shape when heated above a transition temperature. The shape memory material is adapted to move from a first shape to a second shape where it can perform a desired function. In one embodiment of the present invention a method of removing matter from a vessel is described. A catheter with a shape memory material is transported to the site of the matter to be removed. The shape memory material is passed through or around the matter. Heat is utilized to activate the shape memory material and expand the shape memory material. By withdrawing the catheter and the shape memory material through said vessel the matter is carried from the vessel."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a flexible extension for a shape memory polymer occlusion removal device that functions to enhance maneuverability of the shape memory polymer occlusion removal device through tortuous paths en route to the occlusion. The shape memory polymer occlusion removal device can be used to remove non-vascular or vascular occlusions (e.g., blood clot). Such occlusions may include a thrombus (clot), plaque, fatty deposits, and other natural materials as well as fragments of man made devices. An example of an application is blood clot removal following ischemic stroke.

The present invention provides an apparatus for use with a catheter for occlusion removal in a vessel. A shape memory polymer instrument consists of a shape memory polymer actuator operatively connected to the distal end of a transport vehicle for transport through the vessel via a catheter. A flexible elongated unit is operatively connected to the distal end of the shape memory polymer actuator. In one embodiment, the flexible elongated unit is a flexible guide wire. In another embodiment, the flexible elongated unit is a guide wire extension. In one embodiment, the flexible elongated unit comprises wire windings. Another embodiment includes an optical fiber that extends from the transport vehicle and the shape memory polymer actuator surrounds the optical fiber. In one embodiment, the flexible elongated unit is an optical fiber.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
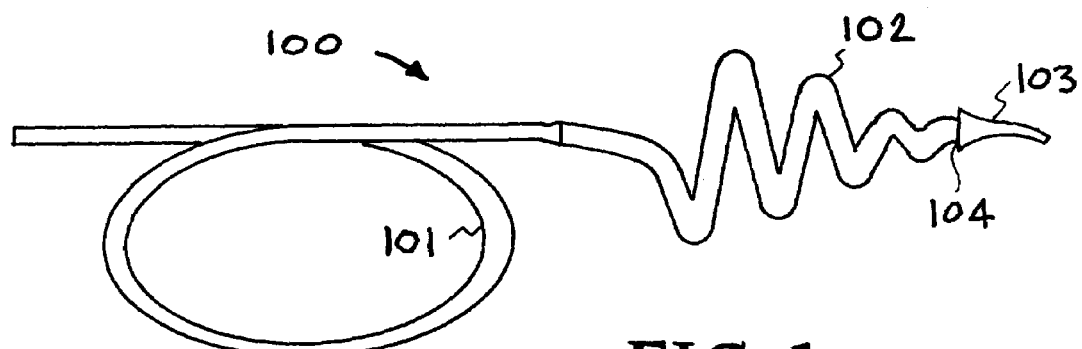
FIG. 1 is a conceptual illustration of an embodiment of the present invention.

Referring now to the drawings and in particular to FIG. 1, a medical application of an embodiment of a guide wire extension for shape memory polymer occlusion removal device constructed in accordance with the present invention is illustrated. The guide wire extension for shape memory polymer occlusion removal device is designated generally by the reference numeral 100. Although a specific application of the present invention is described, it is to be understood that the invention is intended to be general in nature, and can be employed wherever occlusion removal devices are needed. The methods and devices are general to all applications of actuation and control of a shaped memory material device. The invention is not limited to the particular forms disclosed. The invention covers all modifications, equivalents, and alternatives falling within the spirit and scope of the invention as defined by the claims.

The guide wire extension for shape memory polymer occlusion removal device 100 is utilized with a catheter (not shown). The shape memory polymer (SMP) occlusion removal instrument comprises an SMP mechanical actuator 102 attached to the distal end of a transport vehicle 101 for delivery through the vessel via a catheter. The guide wire extension 103 is used to enhance maneuverability of the SMP occlusion removal instrument through tortuous paths (e.g., neurovasculature) en route to the occlusion.

The guide wire extension for shape memory polymer occlusion removal device 100 comprises a flexible guide wire or guide wire-like extension 103. The flexible guide wire or guide wire-like extension 103 is attached to or protrudes from the distal end 104 of the shape memory polymer (SMP) mechanical actuator 102. The shape memory polymer (SMP) mechanical actuator 102 is used to remove non-vascular or vascular occlusions (e.g., blood clot). Such occlusions may include a thrombus (clot), plaque, fatty deposits, and other natural materials as well as fragments of man made devices. An example of an application is blood clot removal following ischemic stroke.

The shape memory polymer (SMP) mechanical actuator 102 uses heat to activate a shape memory material. The shape memory material will change shape when heated above a transition temperature. The shape memory material is adapted to move from a first position to a second position where it can perform a desired function. Shape memory polymer (SMP) mechanical instruments are known, for example shape memory polymer (SMP) mechanical instruments are described in United States Patent Application 2002/0095169 published Jul. 18, 2002 and United States Patent Application 2004/0133231 published Jul. 8, 2004 by Duncan Maitland et al. The disclosures of United States Patent Application 2002/0095169 published Jul. 18, 2002 and United States Patent Application 2004/0133231 published Jul. 8, 2004 are incorporated herein by reference.

The transport vehicle 101 with the shape memory polymer (SMP) actuator 102 is transported via a catheter to the site of the matter to be removed. The shape memory actuator 102 is passed through or around the matter. Heat is utilized to activate the shape memory material and transform the shape memory material. By withdrawing the shape memory polymer (SMP) mechanical instrument through the vessel the matter is carried from the body.

Figure 2:
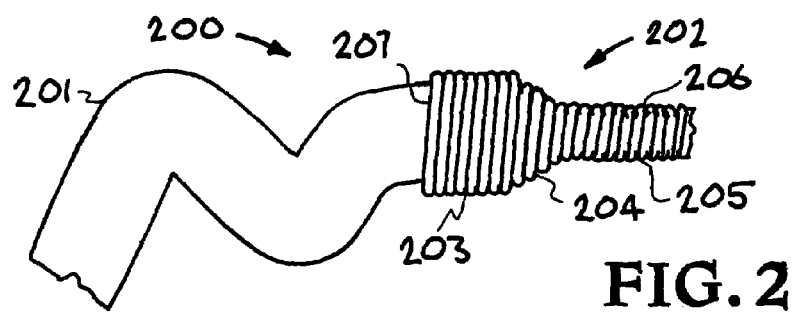
FIG. 2 illustrates another embodiment of the present invention.

Referring now to FIG. 2, another embodiment of a medical application of an embodiment of a guide wire extension for shape memory polymer occlusion removal device constructed in accordance with the present invention is illustrated. This embodiment of the guide wire extension for shape memory polymer occlusion removal device is designated generally by the reference numeral 200.

The guide wire extension device 200 is utilized with a catheter (not shown) in the same manner as the device 100 illustrated in FIG. 1 and previously described. A shape memory polymer (SMP) mechanical actuator 201 is attached to the distal end of a transport vehicle (not shown). The shape memory polymer (SMP) mechanical actuator 201 is a device such as the shape memory polymer (SMP) mechanical instruments described in United States Patent Application 2002/0095169 published Jul. 18, 2002 and United States Patent Application 2004/0133231 published Jul. 8, 2004 by Duncan Maitland et al which are incorporated herein by reference.

The transport vehicle with the shape memory polymer (SMP) actuator 201 is transported to the site of the matter to be removed. The shape memory actuator 201 is passed through or around the matter. Heat is utilized to activate the shape memory material and transform the shape memory material. By withdrawing the transport vehicle and the shape memory polymer (SMP) mechanical actuator 201 through the vessel the matter is carried from the body. The guide wire extension device 200 is used to enhance maneuverability of the SMP occlusion removal instrument 201 through tortuous paths (e.g., neurovasculature) en route to the occlusion.

The guide wire extension device 200 comprises a flexible guide wire-like extension 202. The flexible guide wire-like extension 202 is connected to the distal end 207 of the shape memory polymer (SMP) mechanical actuator 201. The flexible guide wire-like extension 202 is made of wire windings 206. The flexible guide wire-like extension 202 includes an attachment section 203, an elongated guiding section 205, and a transition section 204. The flexible guide wire-like extension 202 is connected to the shape memory polymer (SMP) actuator 201 by overlapping the wire windings 206 of the attachment section 203 of the extension 202 over the distal end 207 of the SMP actuator 201. In one embodiment, the attachment section 203 of the extension 202 is secured to the SMP actuator 201 with epoxy or by another suitable attachment.

Figure 3:
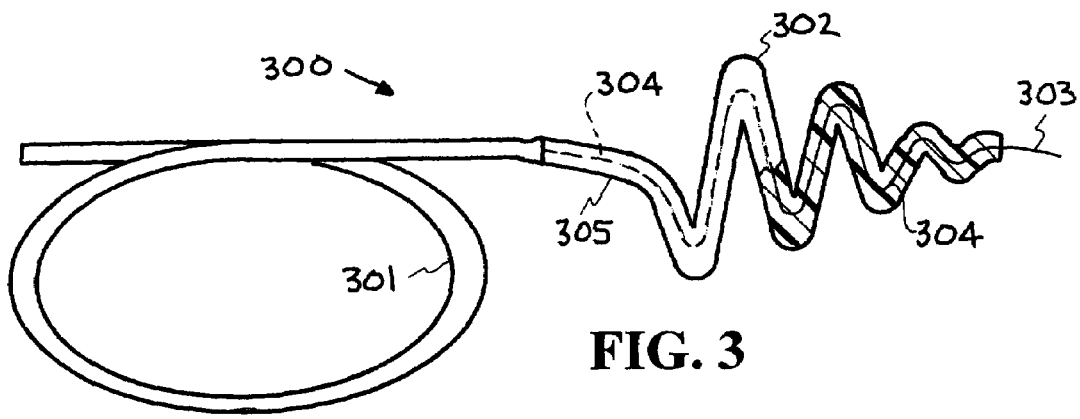
FIG. 3 illustrates yet another embodiment of the present invention.

Referring now to FIG. 3, another embodiment of a medical application of an embodiment of a guide wire extension for shape memory polymer occlusion removal device constructed in accordance with the present invention is illustrated. This embodiment of the guide wire extension for shape memory polymer occlusion removal device is designated generally by the reference numeral 300.

The guide wire extension for shape memory polymer occlusion removal device 300 is utilized with a catheter (not shown) in the same manner as the device 100 illustrated in FIG. 1 and previously described. A shape memory polymer (SMP) mechanical actuator 302 is attached to the distal end of the transport vehicle 301. The guide wire extension device 300 is used to enhance maneuverability of the SMP occlusion removal instrument through tortuous paths (e.g., neurovasculature) en route to the occlusion.

The guide wire extension for shape memory polymer occlusion removal device 300 comprises a flexible guide wire 303. The flexible guide wire 303 is attached to and protrudes from the distal end of the shape memory polymer (SMP) mechanical actuator 302. The flexible guide wire 303 comprises a flexible guide wire connected to the distal end of the shape memory polymer (SMP) mechanical actuator 302.

The shape memory polymer (SMP) mechanical actuator 302 is a device such as the shape memory polymer (SMP) mechanical instruments described in United States Patent Application 2002/0095169 published Jul. 18, 2002 and United States Patent Application 2004/0133231 published Jul. 8, 2004 by Duncan Maitland et al which are incorporated herein by reference. The transport vehicle 301 with the shape memory polymer (SMP) actuator 302 is transported to the site of the matter to be removed. The shape memory actuator 302 is passed through or around the matter. Heat is utilized to activate the shape memory material and transform the shape memory material. By withdrawing the transport vehicle 301 and the shape memory polymer (SMP) mechanical actuator 302 through the vessel the matter is carried from the body.

An optical fiber 304 is carried by the transport vehicle 301. The optical fiber 304 extends beyond the distal end of the transport vehicle 301 and the shape memory polymer (SMP) mechanical actuator 302 comprises a shape memory polymer 305 that surrounds the optical fiber 304. The flexible guide wire 303 is connected to the distal end of the shape memory polymer (SMP) mechanical actuator 302 by connection to the optical fiber 304. In one embodiment, the flexible guide wire 303 is an optical fiber.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for use with a transport vehicle for occlusion removal in a vessel having a tortuous path, comprising:
a shape memory polymer mechanical actuator operatively connected to the transport vehicle for transport through the vessel, said shape memory polymer mechanical actuator activated by heat to change shape from a first shape for transport through the vessel to a second shape for occlusion removal when heated above a transition temperature, said shape memory polymer mechanical actuator having a distal end, and a flexible elongated guide unit operatively connected to said distal end of said shape memory polymer mechanical actuator for enhancing maneuverability of said shape memory polymer mechanical actuator through the tortuous path of the vessel.

2. The apparatus for use with a transport vehicle for occlusion removal in a vessel having a tortuous path of claim 1 wherein said flexible elongated guide unit is a flexible guide wire.

3. The apparatus for use with a transport vehicle for occlusion removal in a vessel having a tortuous path of claim 1 wherein said flexible elongated guide unit is a guide wire extension.

4. The apparatus for use with a transport vehicle for occlusion removal in a vessel having a tortuous path of claim 1 wherein said flexible elongated guide unit includes an elongated guiding section and an attachment section.

5. The apparatus for use with a transport vehicle for occlusion removal in a vessel having a tortuous path of claim 1 wherein said flexible elongated guide unit includes an attachment section operatively connected to said distal end of said shape memory polymer actuator by epoxy.

6. The apparatus for use with a transport vehicle for occlusion removal in a vessel having a tortuous path of claim 1 wherein said flexible elongated guide unit comprises wire windings.

7. The apparatus for use with a transport vehicle for occlusion removal in a vessel having a tortuous path of claim 1 wherein said flexible elongated guide unit includes an attachment section, wherein said flexible elongated guide unit comprises wire windings, and wherein said attachment section is operatively connected to said distal end of said shape memory polymer mechanical actuator by said wire windings being overlapped over said distal end of said shape memory polymer mechanical actuator.

8. The apparatus for use with a transport vehicle for occlusion removal in a vessel having a tortuous path of claim 1 including an optical fiber that extends from the transport vehicle and wherein said shape memory polymer mechanical actuator surrounds said optical fiber.

9. The apparatus for use with a transport vehicle for occlusion removal in a vessel having a tortuous path of claim 1 wherein said flexible elongated guide unit comprises an optical fiber.

10. An apparatus for use with a transport vehicle for occlusion removal in a vessel having a tortuous path, comprising:

shape memory polymer mechanical actuator means for occlusion removal operatively connected to the transport vehicle for transport through the vessel, said shape memory polymer mechanical actuator means activated by heat to change shape from a first shape for transport through the vessel to a second shape for occlusion removal when heated above a transition temperature, said shape memory polymer mechanical actuator means having a distal end, and flexible elongated guide means for guiding said shape memory polymer means through the vessel, said flexible elongated guide means operatively connected to said distal end of said shape memory polymer mechanical actuator means for enhancing maneuverability of said shape memory polymer mechanical actuator through the tortuous path of the vessel.

11. The apparatus for use with a transport vehicle for occlusion removal in a vessel having a tortuous path of claim 10 wherein said flexible elongated guide means is a flexible guide wire.

12. The apparatus for use with a transport vehicle for occlusion removal in a vessel having a tortuous path of claim 10 wherein said flexible elongated guide means is a guide wire extension.

13. The apparatus for use with a transport vehicle for occlusion removal in a vessel having a tortuous path of claim 10 wherein said flexible elongated guide means includes an elongated guiding section and an attachment section.

14. The apparatus for use with a transport vehicle for occlusion removal in a vessel having a tortuous path of claim 10 wherein said flexible elongated guide means includes an attachment section operatively connected to said distal end of said shape memory polymer means by epoxy.

15. The apparatus for use with a transport vehicle for occlusion removal in a vessel having a tortuous path of claim 10 wherein said flexible elongated guide means comprises wire windings.

16. The apparatus for use with a transport vehicle for occlusion removal in a vessel having a tortuous path of claim 10 wherein said flexible elongated guide means includes an attachment section, wherein said flexible elongated guide means comprises wire windings, and wherein said attachment section is operatively connected to said distal end of said shape memory polymer mechanical actuator means by said wire windings being overlapped over said distal end of said shape memory polymer mechanical actuator means.

17. The apparatus for use with a transport vehicle for occlusion removal in a vessel having a tortuous path of claim 10 including an optical fiber that extends from the transport vehicle and wherein said shape memory polymer mechanical actuator means surrounds said optical fiber.

18. The apparatus for use with a transport vehicle for occlusion removal in a vessel having a tortuous path of claim 10 wherein said flexible elongated guide means comprises an optical fiber.

19. An apparatus for use with a transport vehicle for occlusion removal in a vessel having a tortuous path, comprising:

a shape memory polymer mechanical actuator operatively connected to the transport vehicle for transport through the vessel via a catheter, said shape memory polymer mechanical actuator activated by heat to change shape from a first shape for transport through the vessel to a second shape for occlusion removal when heated above a transition temperature, said shape memory polymer mechanical actuator having a distal end, and a flexible elongated guide unit operatively connected to said distal end of said shape memory polymer mechanical actuator for enhancing maneuverability of said shape memory polymer mechanical actuator through the tortuous path of the vessel, said flexible elongated guide unit including an elongated guiding section and an attachment section, wherein said attachment section comprises wire windings with said wire windings overlapped over said distal end of said shape memory polymer mechanical actuator.

20. The apparatus for use with a transport vehicle for occlusion removal in a vessel having a tortuous path of claim 1 wherein said elongated guiding section of said flexible elongated guide unit comprises wire windings.

* * * * *

UNITED STATES PATENT AND TRADEMARK OFFICE
CERTIFICATE OF CORRECTION

PATENT NO. : 7,611,524 B1
APPLICATION NO. : 11/238018
DATED : November 3, 2009
INVENTOR(S) : Duncan J. Maitland, Ward Small, IV and Jonathan Hartman It is certified that error appears in the above-identified patent and that said Letters Patent is hereby corrected as shown below:

Title page, item (73) Assignee: line 6, change "Lawrence Livermore National Security, LLC, Livermore, CA (US)" to --Lawrence Livermore National Security, LLC, Livermore, CA (US) and The Regents of the University of California, Oakland, CA (US)--.

Signed and Sealed this
Second Day of August, 2011

David J. Kappos
*Director of the United States Patent and Trademark Office*